US00PP36923P2

(12) United States Plant Patent
van Swieten

(10) Patent No.: US PP36,923 P2
(45) Date of Patent: Sep. 2, 2025

(54) ***PHALAENOPSIS* PLANT NAMED 'PHA777665'**

(50) Latin Name: *Phalaenopsis hybrida*
Varietal Denomination: PHA777665

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/769,899

(22) Filed: Jul. 11, 2024

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ..... A01H 5/02; A01H 5/00; A01H 6/62
See application file for complete search history.

(56) References Cited

U.S. PATENT DOCUMENTS

PP32,281 P2 * 10/2020 Van Swieten ..... A01H 5/02
Plt./311

OTHER PUBLICATIONS

CPVO Application Consultation Version 4.23.10, retrieved on Apr. 28, 2025 at https://online.plantvarieties.eu/publicConsultationDetails?registerId=20230211&denomination=pha777665, 2 pp. (Year: 2025).*

* cited by examiner

*Primary Examiner* — June Hwu
(74) *Attorney, Agent, or Firm* — C. Anne Whealy

(57) ABSTRACT

A new and distinct cultivar of *Phalaenopsis* plant named 'PHA777665', characterized by its relatively compact and upright plant habit; moderately vigorous growth habit and moderate growth rate; strong flowering stems; strong leaves; freely flowering habit with typically three inflorescences developing per plant, each inflorescence with numerous flowers; white-colored flowers with white and yellow-colored labella; and good postproduction longevity.

2 Drawing Sheets

Figure 1:
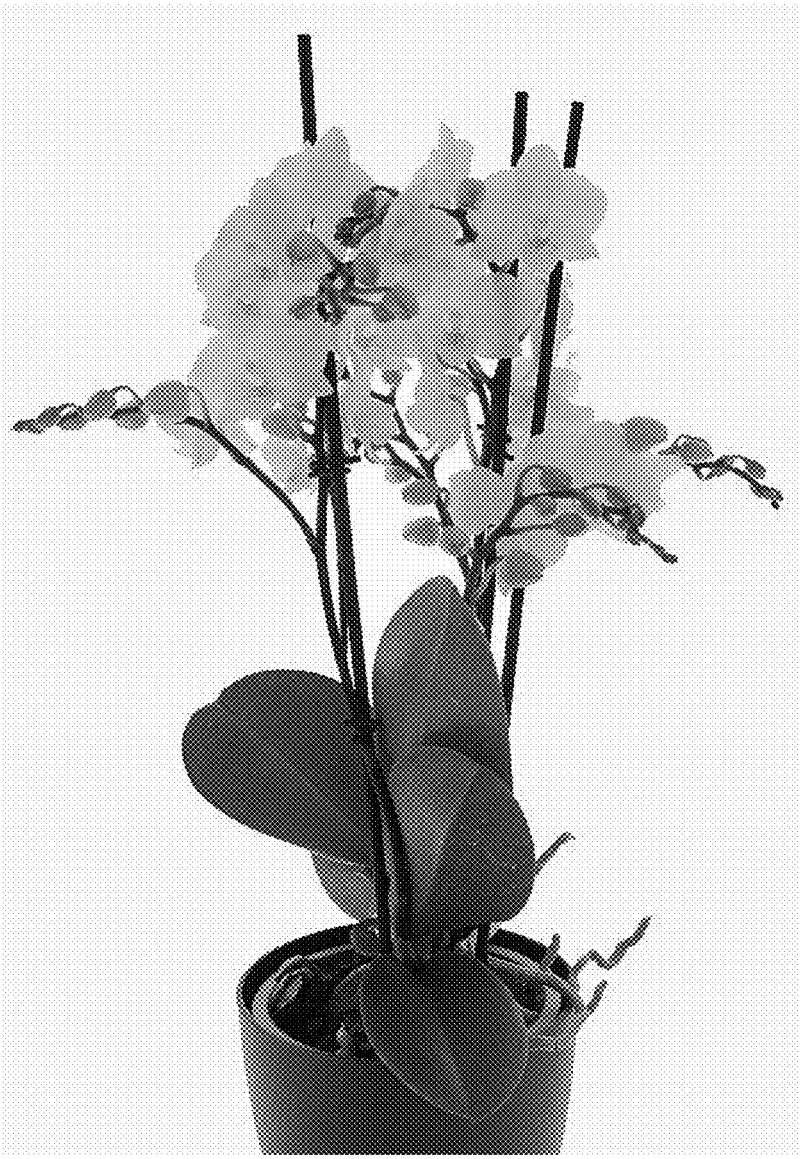

Botanical designation: *Phalaenopsis hybrida.*
Cultivar denomination: 'PHA777665'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B. V. of Bleiswijk, The Netherlands on Jan. 22, 2023, application number 2023/0211. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'PHA777665'.

The new *Phalaenopsis* plant is a product of a planned breeding program conducted by the Inventor in Bleiswijk, The Netherlands. The objective of the breeding program is to develop new compact and freely flowering *Phalaenopsis* plants with flowers with unique and attractive patterns and coloration.

The new *Phalaenopsis* plant originated from a cross-pollination in February 2016 in Bleiswijk, The Netherlands of a proprietary selection of *Phalaenopsis hybrida* identified as code number 00001-3358, not patented, as the female, or seed, parent with *Phalaenopsis hybrida* 'PHALGEPWAL', disclosed in U.S. Plant Pat. No. 30,990, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in December 2018.

Asexual reproduction of the new *Phalaenopsis* plant by in vitro meristem propagation in a controlled environment in Bleiswijk, The Netherlands since December 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA777665'. These characteristics in combination distinguish 'PHA777665' as a new and distinct *Phalaenopsis* plant:

1. Relatively compact and upright plant habit.
2. Moderately vigorous growth habit and moderate growth rate.
3. Strong flowering stems.
4. Strong leaves.
5. Freely flowering habit with typically three inflorescences developing per plant, each inflorescence with numerous flowers.
6. White-colored flowers with white and yellow-colored labella.
7. Good postproduction longevity.

Plants of the new *Phalaenopsis* can be compared to plants of the female parent selection. Plants of the new *Phalaenopsis* differ primarily from plants of the female parent selection in the following characteristics:

1. Leaves of plants of the new *Phalaenopsis* are horizontal to semi-erect whereas leaves of plants of the female parent selection are semi-erect.
2. Petals of plants of the new *Phalaenopsis* are white in color whereas petals of plants of the female parent selection are light purple in color.

Plants of the new *Phalaenopsis* can be compared to plants of the male parent, 'PHALGEPWAL'. Plants of the new *Phalaenopsis* differ primarily from plants of 'PHALGEPWAL' in flower size as plants of the new *Phalaenopsis* are much broader than flowers of plants of 'PHALGEPWAL'.

Plants of the new *Phalaenopsis* can be compared to plants of *Phalaenopsis hybrida* 'PHALGUOCH', disclosed in U.S. Plant Pat. No. 32,281. In side-by-side comparisons, plants of the new *Phalaenopsis* differ primarily from plants of 'PHALGUOCH' in the following characteristics:

1. Leaves of plants of the new *Phalaenopsis* are horizontal to semi-erect whereas leaves of plants of 'PHALGUOCH' are horizontal to semi-dropping.
2. Dorsal sepals of plants of the new *Phalaenopsis* are incurving whereas dorsal sepals of plants of 'PHALGUOCH' are flat and not incurving.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA777665' grown in a container.

Figure 2:
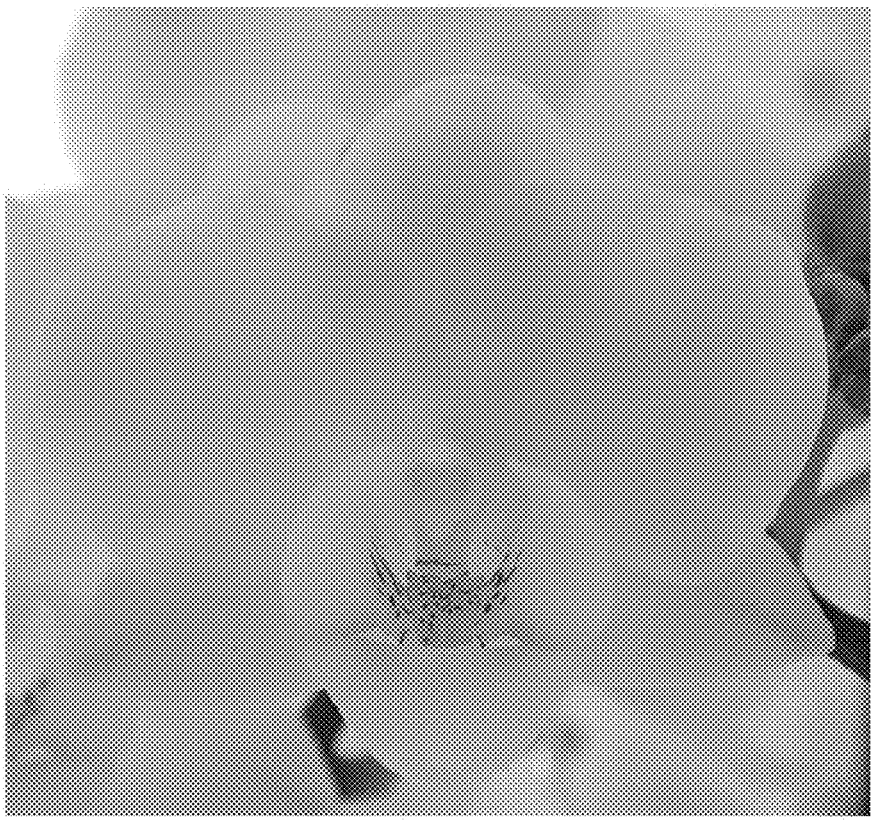

The photograph on the second sheet (FIG. 2) is a close-up view of a typical flower of 'PHA777665'.

DETAILED BOTANICAL DESCRIPTION

The aforementioned photographs and following observations and measurements describe plants grown during the late winter and early spring in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5° C.; and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA777665'.

Parentage:

*Female, or seed, parent.*—Proprietary selection of *Phalaenopsis hybrida* identified as code number 00001-3358, not patented.

*Male, or pollen, parent.*—*Phalaenopsis hybrida* 'PHALGEPWAL', disclosed in U.S. Plant Pat. No. 30,990.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically light green in color; actual color of the roots is dependent on substrate composition, water quality, fertilizer, substrate temperature and age of roots.

*Rooting habit.*—Freely branching; sparse.

Plant description:

*Plant form and growth habit.*—Herbaceous epiphyte; relatively compact and upright plant habit with typically three inflorescences developing per plant, each inflorescence with numerous flowers; monopodial; moderately vigorous growth habit and moderate growth rate.

*Plant height, substrate level to top of foliar plane.*—About 15.6 cm.

*Plant height, substrate level to top of floral plane.*—About 30.4 cm.

*Plant diameter or spread.*—About 27.7 cm.

Leaf description:

*Arrangement and quantity.*—Distichous, simple; sessile; about four to five fully-developed leaves per plant.

*Length.*—About 15.5 cm.

*Width.*—About 6.7 cm.

*Aspect.*—Horizontal to semi-erect.

*Shape.*—Elliptic; slightly carinate.

*Apex.*—Unequal and broadly acute.

*Base.*—Sheathing. Sheath length: About 1.5 cm. Sheath width: About 1.4 cm. Sheath color: Close to 143B; towards the margins, tinged with close to 143A.

*Margin.*—Entire; not undulate.

*Texture and luster, upper and lower surfaces.*—Smooth, glabrous; slightly glossy.

*Venation pattern.*—Camptodromous.

*Color.*—Developing leaves, upper surface: Close to NN137B. Developing leaves, lower surface: Close to 146A slightly tinged with close to 200A. Fully expanded leaves, upper surface: Close to NN137A to NN137B; narrow marginal edge, close to 146A; venation, close to NN137A. Fully expanded leaves, lower surface: Close to a blend of 146A and 146B; towards the margins, close to NN137C; towards the apex, slightly to moderately tinged with close to 200C; venation, close to 146C.

Inflorescence description:

*Appearance and flowering habit*.—Showy zygomorphic flowers arranged on axillary simple or branched racemes; typically three inflorescences develop per plant; each inflorescence with about 27 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about five months after planting; plants flower naturally during the winter into the spring.

*Flower longevity*.—Long flowering period, individual inflorescences maintain good substance for about nine weeks on the plant; flowers not persistent.

*Inflorescence length* (*lowermost flower to inflorescence apex*).—About 19.3 cm.

*Inflorescence width*.—About 15 cm.

*Flower buds*.—Height: About 1.4 cm. Diameter: About 1 cm by 1.2 cm. Shape: Broadly ovate. Color: Close to 145C; towards the apex, tinged with close to 182D.

*Flower size*.—About 4.4 cm (vertical) by 5.3 cm (horizontal).

*Flower depth*.—About 2.3 cm.

*Petals, quantity and arrangement*.—Three, two lateral petals and one center petal transformed into a labellum.

*Lateral petals*.—Length: About 2.7 cm. Width: About 2.8 cm. Shape: Broadly deltoid-ovate. Apex: Obtuse. Margin: Entire; slightly undulate. Texture and luster, upper and lower surfaces: Smooth, glabrous, moderately velvety; matte. Color: When opening, upper surface: Close to 155C; towards the margins and apex, close to NN155C. When opening, lower surface: Close to 157C; towards the margins and apex, close to NN155B; main vein, tinged with close to 186C and 186D. Fully opened, upper surface: Close to NN155D; main vein, slightly tinged with close to 186D; color does not change with subsequent development. Fully opened, lower surface: Close to NN155C to NN155D; main vein, slightly tinged with close to 186D; color does not change with subsequent development.

*Labella*.—Appearance: Three-parted with two lateral lobes and a central lobe. Length, lateral lobes: About 1.6 cm. Width, lateral lobes: About 1.1 cm. Length, central lobe: About 1.7 cm. Width, central lobe: About 4 mm to 17 mm. Length, cirrhose tips: About 2 mm. Shape, lateral lobes: Obovate. Shape, central lobe: Deltoid with a slightly elongated apex. Apex, lateral lobes: Obtuse. Apex, central lobe: Cleft with two upwardly and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 4 mm in length, about 4 mm in width and about 3.5 mm in height. Color: When opening, upper surface: Lateral lobes: Close to NN155C; lower margins, close to 5C; towards the base, axial stripes, close to 181A. Central lobe: Close to NN155D; towards the base, close to 2B and 3B; at the base, close to NN155D and radial stripes, close to 77B and 77C; cirrhose tips, close to NN155D. Callosities: Close to 155C; towards the apex, close to a blend of 4D and 158D and finely dotted with close to 181A. When opening, lower surface: Lateral lobes: Close to NN155C; towards the lower margins, close to 4B. Central lobe: Close to NN155C; towards the base, close to 1C and at the base, close to 155B. Fully opened, upper surface: Lateral lobes: Close to NN155C; lower margins, close to 13B; towards the base, axial stripes, close to 181A. Central lobe: Close to NN155D; towards the base, close to 12B with narrow edges, close to 14A; at the base, close to NN155D and radial stripes, close to N78B; cirrhose tips, close to NN155D. Callosities: Close to 155C; towards the apex, close to 4D and finely dotted with close to 181A. Fully opened, lower surface: Lateral lobes: Close to NN155C; towards the lower margins, close to 13C. Central lobe: Close to NN155C; towards the base, close to 9C and at the base, close to N155D.

*Sepals*.—Quantity and arrangement: Three, one upper dorsal sepal and two lower lateral sepals. Length, dorsal sepal: About 2.6 cm. Width, dorsal sepal: About 1.8 cm. Length, lateral sepals: About 2.6 cm. Width, lateral sepals: About 1.7 cm. Shape, dorsal sepal: Elliptic. Shape, lateral sepals: Ovate. Apex, dorsal sepal: Abruptly acute to shallowly and minutely retuse. Apex, lateral sepals: Bluntly acute. Base, dorsal and lateral sepals: Truncate. Margins, dorsal sepal: Entire; not undulate. Margins, lateral sepals: Entire; lower margins slightly and coarsely undulate. Texture and luster, dorsal and lateral sepals, upper and lower surfaces: Smooth, glabrous, moderately velvety; matte. Color, dorsal sepal: When opening, upper surface: Close to 155C; towards the margins and apex, close to NN155B and NN155C; at the base, slightly tinged with close to 75C. When opening, lower surface: Close to a blend of 145D and 150D; towards the margins and apex, close to 157D; main vein, slightly tinged with close to 75B. Fully opened, upper surface: Close to NN155D; towards the base, slightly tinged with close to 75C. Fully opened, lower surface: Close to a blend of 155C and N155C; main vein, slightly tinged with close to 75B. Color, lateral sepals: When opening, upper surface: Close to 157A and 157B; towards the margins and apex, close to 155C; at the base, sparse fine dots, close to 185D. When opening, lower surface: Close to 145D; towards the margins and apex, close to 157C; main vein, slightly tinged with close to 75A and 75B. Fully opened, upper surface: Close to NN155C to NN155D; towards the base, sparse fine dots, close to 75B. Fully opened, lower surface: Close to 155C; towards the margins and apex, close to NN155C; main vein, slightly tinged with close to 75A and 75B.

*Peduncles*.—Length: About 30.3 cm. Diameter: About 4 mm. Strength: Strong. Aspect: Upright to outwardly arching. Texture and luster: Smooth, glabrous; matte. Color: Close to N200A; heavily dotted with fine dots, close to 147C.

*Pedicels*.—Length: About 3.8 cm. Diameter: About 2.5 mm. Strength: Moderately strong. Aspect: About 45° from peduncle axis. Texture and luster: Smooth, glabrous; matte. Color: Close to 144D; proximally, close to 146A and distally, close to 75B.

*Reproductive organs*.—Androecium: Column length: About 7.5 mm. Column width: About 4 mm. Column color: Close to NN155C and NN155D. Pollinia quantity: Two. Pollinia diameter (per two pollinia): About 2 mm. Pollinia color: Close to 23B. Gynoecium: Stigma length: About 3 mm. Stigma width: About 3.5 mm. Stigma shape: Reniform. Stigma color: Close to NN155D. Ovary length: About 8 mm. Ovary diameter: About 1 mm. Ovary color: Close to 149C. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA777665' as herein illustrated and described.

* * * * *